United States Patent [19]

Bene

[11] Patent Number: 5,744,031

[45] Date of Patent: Apr. 28, 1998

[54] ARTIFICIAL KIDNEY PROVIDED WITH MEANS FOR DETERMINING CHARACTERISTICS OF BLOOD

[75] Inventor: Bernard Bene, Irigny, France

[73] Assignee: Hospal Industrie, France

[21] Appl. No.: 942,460

[22] Filed: Sep. 9, 1992

[30] Foreign Application Priority Data

Sep. 10, 1991 [FR] France ................... 91 11352

[51] Int. Cl.$^6$ ..................... B01D 61/28; B01D 61/32
[52] U.S. Cl. ............... 210/321.71; 210/85; 210/96.2; 210/143; 210/321.65; 210/645; 210/646; 210/647; 210/739; 210/746; 210/929
[58] Field of Search ............................ 210/647, 96.2, 210/74.71, 85, 645, 646, 97, 739, 746, 117, 143, 929, 321.65; 604/4

[56] References Cited

U.S. PATENT DOCUMENTS

| 4,153,554 | 5/1979 | Heide et al. ............. 210/137 |
| 4,209,391 | 6/1980 | Lipps et al. ............ 210/34.65 |
| 4,508,622 | 4/1985 | Polaschegg et al. . |
| 4,683,053 | 7/1987 | Polaschegg ............. 210/321.6 |
| 4,897,184 | 1/1990 | Shoulpice et al. ........... 210/96.2 |
| 4,966,691 | 10/1990 | Brous . |
| 5,024,756 | 6/1991 | Stemby . |
| 5,091,094 | 2/1992 | Veech ................. 210/96.2 |
| 5,100,554 | 3/1992 | Polaschegg ............. 210/647 |

FOREIGN PATENT DOCUMENTS

| 0 097 366 | 1/1984 | European Pat. Off. . |
| 0 330 892 | 9/1989 | European Pat. Off. . |
| 0 428 997 | 5/1991 | European Pat. Off. . |
| 3 436 748 | 7/1985 | Germany . |

OTHER PUBLICATIONS

European Search Report dated May 25, 1992.
English abstract of German Patent No. 3 436 748.

*Primary Examiner*—John Kim
*Attorney, Agent, or Firm*—Finnegan, Henderson, Farabow, Garrett & Dunner, L.L.P.

[57] ABSTRACT

An artificial kidney includes measurement structure for measuring at least one physical characteristic of a fresh dialysis liquid and of used liquid. The measurement structure are disposed in a line portion common to a branch circuit to the feeder line of fresh dialysis liquid and to a branch circuit to the discharge line for the used liquid. Occluding structure permit the liquid to circulate exclusively in one or the other branch circuit. Due to this arrangement, it is possible to obtain the value of the physical characteristics of a patient's blood by calculation as frequently as desired, and to adjust the operation of the kidney permanently to a therapeutic objective set by the physician.

15 Claims, 1 Drawing Sheet

5,744,031

ARTIFICIAL KIDNEY PROVIDED WITH MEANS FOR DETERMINING CHARACTERISTICS OF BLOOD

BACKGROUND OF THE INVENTION

1. Field of the Invention

The invention concerns an artificial kidney permitting an optimized treatment of persons suffering temporarily or chronically from renal insufficiency, and more particularly, a kidney whose operation can be regulated on a continuous basis according to the specific condition and requirements of each patient, taking the physician's prescriptions into account.

2. Description of the Related Art

It is known that apart from their function of purifying certain metabolic waste substances (in particular, urea, creatinine, uric acid) the kidneys also have the function of excreting water and of regulating the electrolytic concentration of the internal environment. As a result, in persons who have lost the use of their kidneys, the system is charged with water which is distributed in the intracellular and extracellular compartments, with salt and impurities, and, moreover, it is generally the seat of an acid-base imbalance.

These patients are treated by means of an artificial kidney according to one or the other, or also a combination of two treatment methods, haemodialysis and haemofiltration. The principle of haemodialysis consists in causing the blood to be purified and a liquid isotonic with blood to circulate on opposite sides of a semipermeable membrane of an exchanger, the impurities migrating through the membrane, from the blood to the dialysis liquid, at a flowrate that is the higher, the greater their concentration in the blood. The principle of haemofiltration consists in withdrawing plasmatic water from the blood by filtration through a semipermeable membrane, the cause of the transfer being this time the difference in the pressures on either side of the membrane.

The quantity of water which must be removed from a chronic patient during each dialysis session can be determined simply by weighing. On the other hand, the prescription of the various dialysis parameters (flow rates of the blood and of the dialysis liquid, concentration of various electrolytes in the dialysis liquid, duration) require an analysis of the blood for determining the concentration of its impurities, the concentration of the excess electrolytes (generally sodium, potassium) and the concentration of the deficient electrolytes (generally bicarbonate).

Conventionally, the analysis of the blood is effected on samples taken from the patient at the start and in the course of the session. This procedure has the drawback of requiring many manipulations and hence being costly and of exposing the persons charged with taking the samples and with performing the analyses to the risks of accidental contamination (hepatitis, aids). Consequently, the number of measurements taken is necessarily reduced and does not always make it possible to adjust the prescription in the course of the treatment in order to bring the patient into the best possible condition at the end of the session.

Methods have therefore been proposed to allow certain characteristics of the blood to be deduced from measurements taken on the dialysis liquid, in particular the concentration of ionized substances in it, whereof sodium represents the preponderant part.

In particular, on the basis of the observation that there is an excellent correlation between the conductivity of the dialysis liquid and the concentration of ionized substances therein, a method has been developed for determining the natremia of a patient consisting in closing the dialysis circuit on itself at regular intervals during the dialysis session and thus forming a loop including the exchanger where a small quantity of dialysis liquid is recirculated until an estimated equilibrium of the concentrations has been obtained on both sides of the membrane. The conductivity of the dialysis liquid is then measured, from which conductivity the concentration of ionized substances, hence sodium, in the blood can be deduced. This method has the disadvantage of reducing the efficiency of the treatment during the periods of recirculation.

On the other hand, U.S. Pat. No. 4,508,622 describes a device for measuring the difference of conductivity between the blood and the dialysis liquid flowing in a dialyzer and for modifying, during the treatment session, the conductivity of the dialysis liquid in order that such difference does not exceed a predetermined value. This device comprises two similar sensors disposed in the circuit of the dialysis liquid upstream and downstream from the dialyzer respectively, whose responses are compared. This device allows the measurements to be taken as frequently as desired and does not disturb the progress of the treatment. However, in addition to not giving any direct information on the conductivity of blood, it has several drawbacks which render its operation difficult, relating substantially to the difficulty of mastering the nonhomologous deviations of the sensors whose response curves are, moreover, never identical, as well as remedying the fouling of the downstream sensor which is permanently immersed in a liquid charged with organic substances coming from the plasma.

A variant of this device partly resolves the problem, since a single sensor is used which is alternately bathed in fresh dialysis liquid and used liquid taken up respectively upstream and downstream from the exchanger. However, this device seems difficult to use in artificial kidneys provided with a device for the volumetric control of ultrafiltration, where the intake and outlet flow rates of the dialysis circuit are kept constant and where a metered quantity of the used liquid is taken up upstream from the outlet corresponding to the quantity of plasmatic water which the physician considers necessary for the patient to lose. Besides, the reliability of this device presupposes that a dialysis liquid is produced whose composition is constant with respect to time, since the sample of the fresh liquid and the sample of the used liquid whose characteristics are measured and compared, have necessarily been produced at different times. Indeed, it goes without saying that if the concentration of the ionized substances in the dialysis liquid is subjected to variations due to the method of preparing the dialysis liquid, which is generally the case when this production is effected on an on-line basis, the comparison of the measurements taken in the fresh dialysis liquid and the used liquid can only provide erroneous data about the composition of the blood plasma. Finally, the taking of samples requires a substantial response time which does not allow precise measurements to be taken in chemically unstable aqueous solutions.

SUMMARY OF THE INVENTION

An object of the invention is to provide an artificial kidney with means for determining characteristics of blood which render possible a reliable measurement of these characteristics, and as frequent as desired, with a view to adjusting the operation of the kidney to a therapeutic objective set by the physician.

In accordance with the invention, this object is attained by means of an artificial kidney comprising:

an exchanger having two compartments separated by a semipermeable membrane, a first compartment being connected to a circuit for extracorporeal circulation of blood, the second compartment being connected to a dialysis liquid circuit having a feeder line for a fresh dialysis liquid connected to an inlet of the second compartment, and a line for the discharge of a used liquid connected to an outlet of the second compartment, measurement means for measuring at least one characteristic of the fresh dialysis liquid and of the used liquid, dialysis liquid circulating means for causing the measurement means to be continuously swept alternately by fresh dialysis liquid and by used liquid, and computing means for calculating at least one characteristic of blood from a corresponding characteristic measured in the fresh dialysis liquid and in the used liquid.

Advantageously, the circulating means for the dialysis liquid includes:

a first branch circuit to the feeder line and a second branch circuit to the discharge line, these branch circuits having a common portion wherein the measurement means are disposed, and occluding means for allowing liquid to circulate exclusively either in one or the other branch circuit.

Thanks to this arrangement of the dialysis liquid circulating means, it is possible to take as many measurements as deemed necessary in the dialysis liquid without any detrimental effect on the efficiency of the treatment, or without any need for extending the duration of the treatment. Moreover, this arrangement allows the measurement means to be permanently swept by the fresh dialysis liquid apart from the brief periods when the characteristics of the used liquid are measured, so that fouling of the measurement means is avoided. Moreover, since the same measurement means are used for the fresh dialysis liquid and the used liquid, one the one hand the measurements are reliable, and, on the other hand, the measurements can be taken on the same sample of dialysis liquid, before and after the flowing thereof in the exchanger, provided that the actuation of the occluding means be properly timed. Finally, although this arrangement does not allow the recirculation of used liquid to be avoided altogether, it makes it at least possible to reduce its volume to negligible values as compared with the total volume of liquid circulating in the dialysis circuit during a treatment session, because after each measurement of the used liquid, only the liquid contained in the line portion recirculates which is common to the branch circuits, and this line portion can be designed with a very small inner volume.

According to one characteristic of the invention, the computing means further calculates from the data delivered by the measurement means the actual clearance of the artificial kidney for a type of impurity such as urea or creatinine.

According to another characteristic of the invention, the measurement means comprises means for measuring the concentration of at least one substance, and the artificial kidney further comprises control means for actuating, according to a comparison between a desired concentration of at least one substance in the blood and the calculated concentration of this substance, means for regulating the flow rate of at least one concentrated solution containing this substance into a reservoir for preparing the dialysis liquid and/or for actuating means for regulating the flow rate of a perfusion liquid containing this substance in the circuit for extracorporeal circulation of blood.

According to another characteristic of the invention, the control means further actuates a circulating pump disposed in the circuit for extracorporeal circulation of blood and/or a circulating pump disposed in the dialysis liquid circuit, according to a comparison between a desired clearance for a type of impurity and the calculated clearance.

According to another characteristic of the invention, the computing means further calculates a duration of the treatment session according to a comparison between a desired clearance and the calculated clearance for a type of impurity, and the control means further actuates means for the extraction of blood filtrate trough the membrane, according to a desired quantity of blood filtrate to be extracted and the calculated duration of the treatment.

BRIEF DESCRIPTION OF THE DRAWINGS

Other characteristics and advantages of the invention will emerge on reading the description that follows. Reference will be made to the attached drawings wherein.

DETAILED DESCRIPTION OF THE PREFERRED EMBODIMENT

Figure 1:
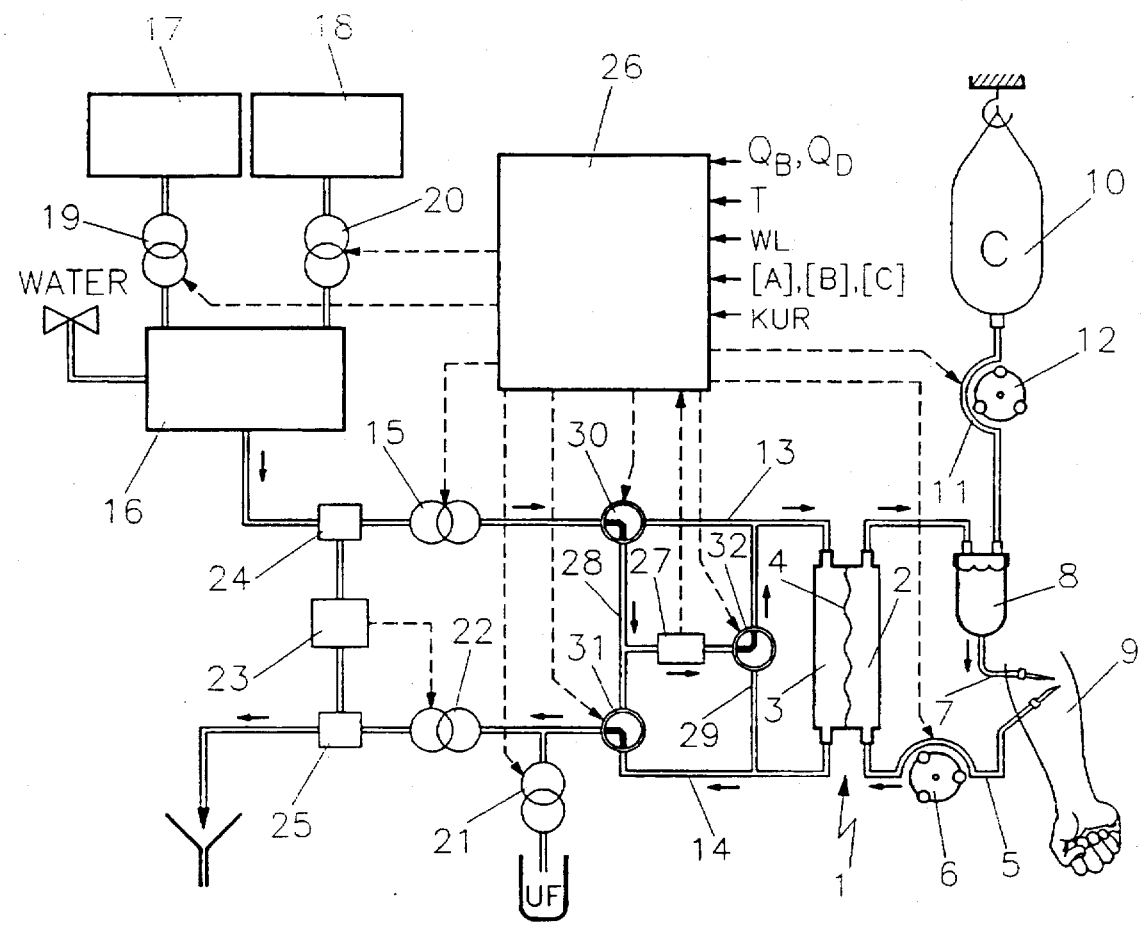
FIG. 1 is a simplified diagram of an artificial kidney in accordance with the invention in a first mode of operation.

The kidney represented in the Figures comprises an exchanger 1 having two compartments 2, 3, separated by a semipermeable membrane 4. A first compartment 2 is connected to a circuit for extracorporeal circulation of blood, including an upstream line 5 connected to an inlet of the compartment 2, wherein there is disposed a circulating pump 6 and a downstream line 7 connected to an outlet of the compartment 2, including a bubble trap 8. The upstream and downstream lines 5, 7 are provided at their free ends with a needle for connecting the artificial kidney to a patient 9. A reservoir 10 containing a sterile perfusion liquid is connected to the bubble trap 8 via a line 11 wherein there is disposed a circulating pump 12.

The second compartment 3 of the exchanger 1 is connected to a dialysis liquid circuit including a feeder line 13 connected at one end to an inlet of the compartment 3 and at its other end to a source of dialysis liquid, and a line 14 for discharging the used liquid, connected at one end to an outlet of the compartment 3 and connected to the drain at its other end. A pump 15 for circulating the dialysis liquid is disposed in the feeder line 13.

The source of the dialysis liquid includes a reservoir 16 for preparing the dialysis liquid connected to a source of water and to one or several reservoirs 17, 18 (two in the Figure, this number not being restrictive) containing concentrated solutions of various compositions. The flow rate of the concentrated solutions into the reservoir 16 can be regulated by means of circulating pumps 19, 20.

The artificial kidney is, moreover, provided with means for taking up and measuring the blood filtrate. These means include an extraction pump 21 mounted so as to draw in used liquid in the discharge line 14 of the dialysis liquid circuit, whilst a second pump 22 is disposed in the discharge line 14 downstream from the extraction pump 21 so as to keep the outflow rate of the used liquid equal to the intake flow of the dialysis liquid imposed by the circulating pump 15. The pump 22 is regulated by a regulating unit 23 according to the comparison of the intake and outflow rates of the dialysis circuit measured by two flow meters 24, 25 disposed respectively upstream from the circulating pump 15 and downstream from the pump 22. Since the intake rate of the fresh dialysis liquid and the outflow rate are kept equal, the quantity of used liquid extracted from the dialysis circuit by the pump 21 is equal to the quantity of the plasmatic water filtered in the exchanger, that is to say, equal to the loss of weight produced in the patient, if the latter does not receive a perfusion of a substitution liquid from elsewhere. This quantity of water is measured by volumetric or weight measuring means (not shown) and the extraction pump 21 is regulated by a control unit 26, according to the comparison of a desired rate of ultrafiltration WL/T and the measured rate of ultrafiltration.

In accordance with the invention, this artificial kidney is provided with means for measuring one or more characteristics (conductivity, pH, temperature, for example) of the dialysis liquid and of the used liquid from which it is possible to calculate the corresponding characteristics of the blood. These measurement means include one or more sensors 27 disposed in a line portion common to a first branch circuit 28 to the feeder line 13 and a second branch circuit 29 to the discharge line 14. Occlusion means constituted by three three-way valves 30, 31, 32 are disposed in the dialysis liquid circuit and its branch circuit for allowing the circulation of liquid exclusively in either the one or the other branch circuit.

Figure 2:
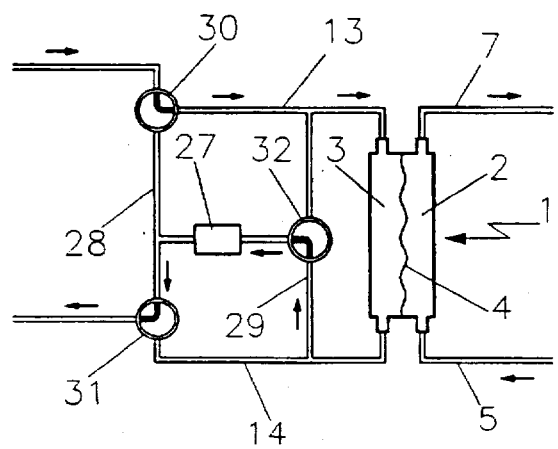
FIG. 2 shows a detail of the artificial kidney represented in FIG. 1 in a second mode of operation.

In greater detail, a first valve 30 is disposed at the junction of the feeder line 13 and of the upstream end of the first branch circuit 28 with reference to the direction of circulation of the dialysis liquid. In a first position, the valve 30 constrains the fresh dialysis liquid to circulate in the first branch circuit 28 (FIG. 1), and in a second position, this valve cuts the communication between the feeder line 13 and its branch circuit (FIG. 2). A second valve 31 is disposed at the junction of the discharge line 14 and of the downstream end of the second branch circuit 29 with reference to the direction of circulation of the used liquid. In a first position, the valve 31 cuts the communication between the discharge line 14 and its branch circuit (FIG. 1) and in a second position, this valve constrains the used liquid to circulate from the second branch circuit 29 in the portion of the discharge line 14 situated downstream from the valve 31 (FIG. 2). A third valve 32 is disposed in the line portion common to the two branch circuits 28, 29 downstream (respectively upstream) from the measurement means 27 with reference to the direction of circulation of the fresh dialysis liquid (respectively of the used liquid). In a first position, the valve 32 inhibits the circulation of liquid in the second branch circuit 29 and permits the circulation of liquid in the first branch circuit 28 (FIG. 1), and vice versa, in a second position (FIG. 2).

To sum up, when the valves 30, 31, 32 are in the first position (FIG. 1), the fresh dialysis liquid passes into the first branch circuit 28 and sweeps the sensors 27, while the used liquid circulates exclusively in the discharge line 14. And when the valves are in the second position (FIG. 2), the fresh dialysis liquid circulates exclusively in the feeder line 13, while the used liquid passes into the second branch circuit 29 and sweeps the sensors 27.

In accordance with the invention, the signals delivered by the sensors 27 are supplied to the computing and control unit 26 which controls the artificial kidney according to the parameters which it calculates, such as certain characteristic values of the blood (the concentration of ionized substances, of bicarbonate for example) as well as the performance of the artificial kidney (dialysance, clearance for a given substance) and according to the data which are supplied to it by an operator prior to the treatment session, such as the duration T of the session, the flow rates of the blood QB and of the dialysis liquid QD, the desired loss of weight WL, the desired concentration [A], [B], [C] of electrolytes A, B, C in the blood, and in particular, the desired clearance of urea KUR.

The operation of the artificial kidney described above is as follows.

Before the start of a treatment session, an operator provides the computing and control unit 26 with the necessary data for controlling the artificial kidney, that is to say, the composition of the dialysis liquid with electrolytes A and B, the delivery rate QB of the circulating pump 6 for the blood, the delivery rate QD of the circulating pump 15 for the dialysis liquid, the desired loss of weight WL and the duration set beforehand for the treatment session T. These data correspond to the physician's prescriptions which are drawn up in accordance with the condition of the given patient by an initial weighing and blood analysis.

First of all, a quantity of dialysis liquid sufficient for starting the treatment is prepared by mixing and heating in the reservoir 16 water and the concentrated solutions A, B. The dialysis liquid may contain the main electrolytes of the blood (sodium, potassium, magnesium, calcium, bicarbonate, chloride) or lack some of them, bicarbonate for example. In the latter case, a bicarbonate solution will be perfused to the patient in the course of the treatment session by means of the perfusion device 10, 11, 12 to compensate the diffusion losses in the exchanger 1 and optionally to act on the patient's acid-base balance.

Once the reservoir 16 has been filled with dialysis liquid ready for use and after the various circuits of the artificial kidney have been rinsed and filled, and the circuit 5, 7 for extracorporeal circulation of the blood has been connected to the patient 9, all the pumps of the artificial kidney are started and/or adjusted to the flow rates stored in the memory in the unit 26 beforehand.

Measurements are then taken in the dialysis liquid during the whole treatment session by means of the sensors 27. In the discussion that follows, a conductivity probe will be taken as an example to explain the operation of the artificial kidney, while the choice of this particular sensor must, of course, not be taken to be restrictive.

In accordance with the invention, the signal delivered by the conductivity probe, in respect of which the close correlation of the conductivity and the concentration of ionized substances sweeping the probe has been recalled above, is first of all used to determine the patient's natremia. To do this, one programs the consecutive passing into the exchanger 1 of two volumes of dialysis liquid having different conductivities so as to measure by means of a switch-over of the three-way valves 30, 31, 32 in each pass from the first to the second position, four conductivity values $CDi1$, $CDo1$, $CDi2$, $CDo2$ (respectively the conductivity of the dialysis liquid at the inlet and outlet of the exchanger during the first pass and the second pass) from which the unit 26 can calculate the concentration $CBi$ of ionized substances in the patient's blood at the inlet of the exchanger by application of the formula:

$$CBi = \frac{CDo2 \times CDi1 - CDo1 \times CDi2}{(CDi1 - CDo1) - (CDi2 - CDo2)}$$

this formula being derived from the general formula of the dialysance D of an artificial kidney for a given substance, which is defined as being equal to the ratio between the mass transfer for this substance QD X (CDi–CDo) and the gradient of the concentration of this substance between the blood and the dialysis liquid at the inlet of the exchanger CBi–CDi.

The unit 26 then compares the concentration of ionized substances in the patient's blood (whereof sodium represents the preponderant part) with the desired concentration previously stored in its memory, and if required, actuates the pump 19 or 20 to increase or reduce the flow rate of the concentrated solution containing sodium, that is to say, with all things remaining otherwise equal, to increase or reduce the sodium content of the dialysis liquid.

Moreover, in accordance with the invention, the unit 26 calculates by extrapolation on the basis of the dialysance for sodium, and according to known rules of correspondence, the clearance of the urea which is a representative value of the purifying efficiency of the artificial kidney, depending both on the characteristics of the exchanger (nature and surface of the membrane) and the flow rates of the blood and of the dialysis liquid in the exchanger. The unit 26 then compares this clearance calculated for the urea with the desired clearance KUR and if required, either modifies the duration of the initially programmed treatment session or modifies the delivery of the circulating pump 15 for the dialysis liquid or the delivery of the circulating pump 6 for the blood circulation. In the first case, the unit 26 modifies the delivery of the pump 21 for extraction of the blood filtrate to take into account the prolongation or shortening of the dialysis session, the instruction for the weight loss WL remaining otherwise unaltered.

When the measurement means 27 include a pH probe and a CO2 partial pressure probe, the unit 26 calculates the concentration of bicarbonate in the blood. If one of the concentrated solutions A or B contains bicarbonate, the unit 26 modifies the bicarbonate content of the dialysis liquid by modifying the delivery of one of the pumps 19 or 20 when the bicarbonate concentration in the blood differs from the desired concentration. If the dialysis liquid does not contain bicarbonate, then the bicarbonate is supplied to the patient is effected by perfusion as mentioned above, and when the result of the comparison effected by the unit 26 shows a difference between the measured bicarbonate concentration and the desired concentration, the unit increases or reduces the delivery of the perfusion pump 12.

The invention is not restricted to the mode of embodiment described above and can accommodate variants. In particular, it goes without saying that the operation of the artificial kidney dialysis circuit would not be modified if the measurement means were to comprise selective detectors for a given substance instead of a conductivity probe and/or a pH probe.

I claim:

1. An artificial kidney comprising:
    an exchanger having two compartments separated by a semipermeable membrane, a first compartment being connected to a circuit for extracorporeal circulation of blood having a circulating pump disposed therein, a second compartment being connected to a dialysis liquid circuit;
    measurement means for measuring data corresponding to at least one physicochemical characteristic of a fresh dialysis liquid and at least one physicochemical characteristic of a used liquid;
    computation means responsive to data received from the measurement means for calculating an actual clearance of the artificial kidney for a type of impurity; and
    control means for controlling a flow rate through the extracorporeal blood circuit as a function of a comparison between the calculated clearance and a predetermined clearance.

2. The artificial kidney according to claim 1, wherein the dialysis liquid circuit comprises:
    a feeder line connected to an inlet of the second compartment for supplying the fresh dialysis liquid, and a discharge line connected to an outlet of the second compartment for discharging the used liquid;
    a first branch circuit connected to the feeder line, and a second branch circuit connected to the discharge line, the first and second branch circuits having a common portion wherein the measurement means are disposed; and
    occluding means for allowing liquid to circulate exclusively in either one of the first and second branch circuits.

3. The artificial kidney according to claim 2, wherein the occluding means includes:
    a first three-way valve for establishing exclusive communication between the feeder line and the first branch circuit, the first three-way valve being disposed upstream from the measurement means with respect to a direction of flow of the fresh dialysis liquid;
    a second three-way valve for establishing exclusive communication between the discharge line and the second branch circuit, the second three-way valve being disposed downstream from the measurement means with respect to a direction of flow of the used liquid; and
    a third three-way valve for causing the common portion to communicate either with the feeder line disposed downstream from the measurement means with respect to the direction of flow of the fresh dialysis liquid, or to communicate with the discharge line disposed upstream from the measurement means with respect to the direction of flow of the used liquid.

4. The artificial kidney according to claim 1, wherein the measurement means comprises means for measuring conductivity.

5. The artificial kidney according to claim 1, wherein the measurement means comprises means for measuring pH and a partial pressure of $CO_2$.

6. An artificial kidney comprising:
    an exchanger having two compartments separated by a semipermeable membrane, a first compartment being connected to a circuit for extracorporeal circulation of blood, a second compartment being connected to a dialysis liquid circuit having a circulating pump disposed therein;
    measurement means for measuring data corresponding to at least one physicochemical characteristic of a fresh dialysis liquid and at least one physicochemical characteristic of a used liquid;
    computation means responsive to data received from the measurement means for calculating an actual clearance of the artificial kidney for a type of impurity; and
    control means for controlling a flow rate through the dialysis liquid circuit as a function of a comparison between a predetermined clearance for the type of impurity and the calculated clearance.

7. The artificial kidney according to claim 6, wherein the dialysis liquid circuit comprises:
- a feeder line connected to an inlet of the second compartment for supplying the fresh dialysis liquid, and a discharge line connected to an outlet of the second compartment for discharging the used liquid;
- a first branch circuit connected to the feeder line, and a second branch circuit connected to the discharge line, the first and second branch circuits having a common portion wherein the measurement means are disposed; and
- occluding means for allowing liquid to circulate exclusively in either one of the first and second branch circuits.

8. The artificial kidney according to claim 7, wherein the occluding means includes:
- a first three-way valve for establishing exclusive communication between the feeder line and the first branch circuit, the first three-way valve being disposed upstream from the measurement means relative to a direction of flow of the fresh dialysis liquid;
- a second three-way valve for establishing exclusive communication between the discharge line and the second branch circuit, the second three-way valve being disposed downstream from the measurement means relative to a direction of flow of the used liquid; and
- a third three-way valve for causing the common portion to communicate either with the feeder line disposed downstream from the measurement means relative to the direction of flow of the fresh dialysis liquid, or to communicate with the discharge line disposed upstream from the measurement means relative to the direction of flow of the used liquid.

9. The artificial kidney according to claim 6, wherein the measurement means includes means for measuring conductivity.

10. The artificial kidney according to claim 6, wherein the measurement means includes means for measuring pH and a partial pressure of $CO_2$.

11. An artificial kidney comprising:
- an exchanger having two compartments separated by a semipermeable membrane, a first compartment being connected to a circuit for extracorporeal circulation of blood, second compartment being connected to a dialysis liquid circuit;
- extraction means for extracting a blood filtrate through the membrane from the first compartment into the second compartment;
- measurement means for measuring data corresponding to at least one physicochemical characteristic of a fresh dialysis liquid and at least one physicochemical characteristic of a used liquid;
- computation means responsive to data received from the measurement means for calculating an actual clearance of the artificial kidney for a type of impurity, and for calculating a duration of a treatment session according to a comparison between a predetermined clearance and the calculated clearance; and
- control means for controlling the extraction means as a function of a desired quantity of blood filtrate to be extracted, and as a function of the calculated duration of the treatment session.

12. The artificial kidney according to claim 11, wherein the dialysis liquid circuit comprises:
- a feeder line connected to an inlet of the second compartment for supplying the fresh dialysis liquid, and a discharge line connected to an outlet of the second compartment for discharging the used liquid;
- a first branch circuit connected to the feeder line, and a second branch circuit connected to the discharge line, the first and second branch circuits having a common portion wherein the measurement means are disposed; and
- occluding means for allowing liquid to circulate exclusively in either one of the first and second branch circuits.

13. The artificial kidney according to claim 12, wherein the occluding means includes:
- a first three-way valve for establishing exclusive communication between the feeder line and the first branch circuit, the first three-way valve being disposed upstream from the measurement means with respect to a direction of flow of the fresh dialysis liquid;
- a second three-way valve for establishing exclusive communication between the discharge line and the second branch circuit, the second three-way valve being disposed downstream from the measurement means with respect to a direction of flow of the used liquid; and
- a third three-way valve for causing the common portion to communicate either with the feeder line disposed downstream from the measurement means with respect to the direction of flow of the fresh dialysis liquid, or to communicate with the discharge line disposed upstream from the measurement means with respect to the direction of flow of the used liquid.

14. The artificial kidney according to claim 11, wherein the measurement means comprises means for measuring conductivity.

15. The artificial kidney according to claim 11, wherein the measurement means comprises means for measuring pH and a partial pressure of $CO_2$.

* * * * *